United States Patent [19]

Stelzer et al.

[11] Patent Number: 5,003,108
[45] Date of Patent: Mar. 26, 1991

[54] PROCESS FOR THE PREPARATION OF PHOSPHANES

[75] Inventors: Othmar Stelzer; Klaus-Peter Langhans, both of Wuppertal; Jürgen Svara, Köln; Norbert Weferling, Hürth, all of Fed. Rep. of Germany

[73] Assignee: Hoechst Aktiengesellschaft, Werk-Knapsack, Fed. Rep. of Germany

[21] Appl. No.: 449,137

[22] Filed: Dec. 11, 1989

Related U.S. Application Data

[63] Continuation of Ser. No. 240,099, Sep. 2, 1988, abandoned.

[30] Foreign Application Priority Data

Sep. 18, 1987 [DE] Fed. Rep. of Germany ....... 3731424

[51] Int. Cl.$^5$ ................................. C07F 9/50
[52] U.S. Cl. ...................................... 568/8
[58] Field of Search ........................ 568/8, 17

[56] References Cited

U.S. PATENT DOCUMENTS 4,073,810 2/1978 Hestermann et al. .

FOREIGN PATENT DOCUMENTS

| 2727390 | 1/1979 | Fed. Rep. of Germany . | |
|---|---|---|---|
| 11934 | 7/1967 | Japan | 568/17 |
| 1016291 | 5/1983 | U.S.S.R. | 568/17 |
| 928207 | 6/1963 | United Kingdom | 568/17 |

OTHER PUBLICATIONS

Houben–Weyl, "Methoden zur Herstellung und Umwandlung von Phosphinen . . .", Methoden der Organischen Chemie, vol. XII/1, 1963, p. 17.
Jolly, William L. et al., *Inorganic Synthesis* 11, 124 (1968).

*Primary Examiner*—Gary P. Straub
*Assistant Examiner*—Stuart L. Hendrickson
*Attorney, Agent, or Firm*—Connolly and Hutz

[57] ABSTRACT

For the preparation of phosphanes, phosphane and alkyl halides are reacted in the presence of alkali metal hydroxide solutions and tetraalkylammonium or tetraalkylphosphonium salts as the catalysts.

10 Claims, No Drawings

PROCESS FOR THE PREPARATION OF PHOSPHANES

This application is a continuation of application Ser. No. 240,099, filed Sep. 2, 1988 now abandoned.

The present invention relates to a process for the preparation of phosphanes of the general formulae

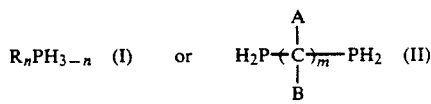

$$R_n PH_{3-n} \quad (I) \quad \text{or} \quad H_2P\text{-}(C(A)(B))_m\text{-}PH_2 \quad (II)$$

in which R represents a straight-chain or branched alkyl group having 1 to 24 carbon atoms or a cycloalkyl, benzyl or allyl group, n is 1 or 2, m corresponds to 2, 3 or 4 and A and B are identical or different and have either the meaning or R, hydrogen or a phenyl group.

This process consists in the reaction of phosphane in the presence of a catalyst with reagents of the general formula Rhal or hal(C(A)(B))$_m$hal, in which R, A, B and m have the meaning mentioned and hal stands for chlorine or bromine.

Organophosphorus compounds are becoming increasingly important in industry as herbicides, ligands in catalysts for hydroformylation (oxo synthesis), phase transfer catalysts (as phosphonium salts) and extractants (as tertiary phosphane oxides and phosphinic acids). Phosphane which can be easily prepared by means of known processes in industrial quantities is used as the building block for the synthesis of these classes of compounds.

By the prior art, trialkylphosphanes are available without difficulty by radical-initiated addition of $PH_3$ to olefinic double bonds.

The controlled preparation of primary and secondary alkylphosphanes is considerably more difficult. Therefore, there has been no shortage of proposals to obtain these phosphanes; in particular, the reaction of $PH_3$ with alkylhalides over noble metal catalysts or activated carbon has already been attempted (DE 2,407,461 A1). All prior art methods have disadvantages such as, for example, poor yields or undesired side products, which prevented their application in industry.

Surprisingly, it has now been found that the disadvantages of the known processes can be avoided, if a tetraalkylammonium or tetraalkylphosphoium salt is used as the catalyst in the reaction of phosphane with alkyl halides and the reaction is carried out in the presence of an aqueous alkali metal hydroxide solutions at temperatures between $-20°$ C. and $200°$ C. and at a pressure of 0 to 10 bar, in which process for each mole of hal at least one mole of alkali metal hydroxide is used.

Advantageous reinforcement of the process according to the invention are: working in the presence of inert organic solvents; carrying out the reaction at temperatures between 0 and $50°$ C.; using the catalyst in concentrations from 0.1 to 5 mole %, based on the $PH_3$ used; using aliphatic or aromatic hydrocarbons having 5-16 carbon atoms, individually or as a mixture, as the inert organic solvent and using aqueous NaOH or KOH solution having a concentration of 50–70% by weight as the alkali metal hydroxide solution. In this reaction, the phosphane is deprotonated with concentrated aqueous alkali metal hydroxide solution. This process is critically dependent on the use of the catalyst in the form of an ammonium or phosphonium salt. Without such a catalyst, there is virtually no reaction. In some cases, it is advantageous to dispense completely with the use of an inert organic solvent. In the reaction of $PH_3$ with methyl chloride, for example, the reaction products methylphosphase and possibly dimethylphosphane can be recovered directly on completion of the reaction by releasing the autoclave and subsequent gentle heating. The isolation of the products in the form of their hydrogen phosphonium salts is achieved in the known manner by passing the reaction gas through wash bottles containing dilute HCl (asbsorbs only methylphosphane) and/or concentrated HCl (absorbs $(CH_3)_2PH$, $CH_3PH_2$ and $(CH_3)_3P$). At the same time, excess methyl chloride and $PH_3$ may still be present in the gas. By adding an appropriate amount of alkali metal hydroxide, the phosphanes can be liberated again in a controlled fashion. The process according to the invention is particularly suitable for the monoalkylation of $PH_3$. The specificity and simplicity of the process are not achieved by any other known process. Furthermore, only relatively low-priced reagents are used. However, the preparation of dialkylated products is also possible, although in this preparation the removal and recycling of monoalkylated product is recommended. Thus, for example $(CH_3)_2PH$ can be obtained, a compound whose structural simplicity is in stark contrast to the difficulty of its past preparation.

Especially in these cases where alkyl halides which are gaseous under standard conditions (methyl chloride, ethyl chloride), are used, it is advantageous to carry out the reaction in an autoclave under pressure (Examples 1–3, method A). In principle, all reactions can be carried out by method A (see Example 4).

According to method B, the reaction is carried out under atmospheric pressure or at so small a pressure (250 mbar) that the reactions can be carried out in standard glass apparatuses.

General operating conditions for method A (amounts specified in Table 1). $PH_3$ was condensed at $-40°$ C. into a 5-liter autoclave. Alkyl halide was then added, either also by condensing in or by pumping in. At cooling water temperature, a solution of 450 g of KOH (85%) in 300 g of $H_2O$ (=52% of total concentration of KOH in $H_2O$) was pumped in. The reaction was initiated by metering a solution of the catalyst either in toluene or water into the reaction vessel. $PH_3$/methyl chloride mixtures were worked by letting down the gas phase of the autoclave through 2 wash bottles containing each 250 g of concentrated HCl. At the same time, the autoclave was heated to $50°$ C. A further 200 g of $H_2O$ was then pumped into the reactor and the aqueous phase was separated from the organic phase (exception: example 3). For analysis or percentage determination, $^{31}$P-NMR spectra of both the toluene phase and also the HCl wash solution were recorded and also elemental phosphorus analyses of these samples were also carried out. In the KOH/$H_2O$ phase, no phosphorus could be detected ($<0.1\%$). The $PH_3$/methyl chloride reaction products are characterized by the following $^{31}$P-NMR data:

$CH_3PH_2$: $-161$ ppm, $^1J_{PH}=188$ Hz, triplet (in toluene) $-65.5$ ppm (as $MePh_3Cl^-$ in HCl/$H_2O$).

$(CH_3)_2PH$: $-99$ ppm, $^1J_{PH}=186$ Hz, doublet (in toluene) $-34.5$ ppm, $^1J_{PH}=495$ Hz, triplet (as $Me_2PH_2Cl^-$ in HCl/$H_2O$).

$(CH_3)_3P$: $-62.6$ ppm (in toluene) $-5.8$ ppm, $^1J_{PH}=505$ Hz, doublet (as $me_3PH\ Cl^-$ in Hcl/$H_2O$).

$(CH_3)_4P^+Cl^-$: +24 ppm (toluene).
$(CH_3)_3P(:O)$: +39 PPm (toluene).

agent. The aqueous phase was then diluted with water in a 1 : 1 ratio, and the organic phase was separated off,

TABLE 1

Reaction of $PH_3$ with alkyl halides under pressure

| Example | $PH_3$ g (mol) | Alkyl-halide g (mol) | Solvent | Reaction conditions | Distribution of products — HCl absorber solution | Distribution of products — Toluene Phase | Degree of conversion | Products |
|---|---|---|---|---|---|---|---|---|
| 1 | 61 (1.8) | 60 (1.8) Methyl chloride | — | 2 h/15–20° C. Pmax.: 9–1 bar Final pressure: 5.0 bar Catalyst: Tetraoctylphosphonius. bromide 10 g | $CH_3PH_2$: 94 Mol % $(CH_3)_2PH$: 5 Mol % Others: <1 Mol % | — | >98%, based on $CH_3Cl$ used | $CH_3PH_2$: 66 g $(CH_3)_2PH$: 4 g |
| 2 | 38 (1.1) | 261 (5.4) Methyl chloride | Toluene 450 ml | 2 h/15–25° C. 18 h/15° C. Pmax.: 4.1 bar Final pressure: 0.5 bar Catalyst: $(C_4H_9)_3C_{16}H_{33}PBr$ 10 g in 50 ml Toluene | $CH_3PH_2$: 7.5 Mol % $(CH_3)_2PH$: 91 Mol % $(CH_3)_3P$: 1.5 Mol % $^+(CH_3)_4PCl^-$: — | <0.1 Mol % 90.6 Mol % 2.9 Mol % 6.6 Mol % | >99%, based on $PH_3$ used | $CH_3PH_2$: 2 g $(CH_3)_2PH$: 63 g $(CH_3)_3P$: 2 g $(CH_3)_4PCl$: 4 g |
| 3 | 37 (1.1) | 153 (3.2) Methyl chloride | — | 5 h/15–15° C. 18 h/18° C. Pmax.: 7.4 bar Final pressure: 2.6 bar 10 g $(C_4H_9)_3C_{16}H_{33}PBr$ dissolved in $H_2O$/KOH | $CH_3PH_2$: 64 Mol % $(CH_3)PH$: 35 Mol % $(CH_3)_3P$: 0.5 Mol % | — | 93%, based on $PH_3$ used | $CH_3PH_2$: 32 g $(CH_3)_2P$: 23 g $(CH_3)_3P$: 0.5 g |
| 4 | 71 (2.1) | 520 (1.8) Hexadecyl bromide | Toluene 500 ml | 3 h/10–25° C. 3 h/80° C. Pmax.: 8.8 bar Final pressure: 0.8 bar 15 g $(C_4H_9)_3C_{16}H_{33}PBr$ | — | $C_{16}H_{33}PH_2$: 97 Mol % 31-NMR: −139 ppm | 74%, based on $PH_3$ used | $C_{16}H_{33}PH_2$ about 389 g (84%, based on RHal) |

General operating conditions for method B (Examples 5–7)

$[NBu_4]^+Cl^-$(tetra-n-butylammonium chloride) were added to the amounts of 56% strength aqueous solution of KOH listed in Table 2. After $N_2$ had been passed through the solutions, $PH_3$ was passed over the solution (pressure 250 mbar) and the appropriate alkylating agent was added dropwise at 10°–20° C. (reaction conditions a). After the addition was completed, stirring was continued for 1–2 hours at 40° C. (reaction conditions b) to obtain complete conversion of the alkylating agent. The aqueous phase was then diluted with water in a 1 : 1 ratio, and the organic phase was separated off, washed twice with 100 ml of $H_2O$ each time and dried over $Na_2SO_4$. Fractional distillation gave the primary phosphanes. (See Table 2 for amounts of reagents, yields, reaction conditions see Table 2).

TABLE 2

Alkylation of $PH_3$ with RX and phase transfer catalysis

| | Example 5 | Example 6 | Example 7 |
|---|---|---|---|
| | $CH_3-(CH_2)_3-PH_2$ | $H_2C{=}CH{-}CH_2{-}PH_2$ | cyclic: $H_2C(CH_2)(CH_2)(H_2P)(PH_2)$ |
| RX g (mol) | $CH_3-(CH_2)_3-Cl$ 9.26 (0.1) | $H_2C{=}CH{-}CH_2{-}Cl$ 76.5 (1.0) | $Cl-(CH_2)_3Cl$ 28.2 (0.25) |
| $(C_4H_9)_4N^+Cl^-$ g (mol) | 2.8 (0.001) | 13.9 (0.05) | 7.0 (0.025) |
| 56% KOH g (mol) | 20.0 (0.2) | 200.0 (2.0) | 100 (1.0) |
| Organic Phase | 100 ml Pentane | 200 ml n-Octane | 200 ml Petroleum ether 40/60 |
| Reaction conditions | (a) 1 h/20° C. (b) 1 h/40° C. | (a) 2 h/10° C. (b) 1 h/40° C. | (a) 1 h/20° C. (b) 2 h/40° C. |
| Yield g (%) | 7.9 (88) | 41.0 (55) | 24.0 (89) |
| B.p. °C. | 86 | 66 | 92/50 mbar |

We claim:
1. A process for the preparation of a phosphine of the formula

$$R-PH_2$$

in which R is a straight chain or branched alkyl group having from 1 to 24 carbon atoms comprising reacting phosphine (PH$_3$) with a reagent of the formula R-hal wherein R has the meaning mentioned and hal is chlorine or bromine, wherein a catalyst selected from the group consisting of tetraalkylammonium and tetraalkylphosphonium salt is added to the reactants, and the reaction is conducted in the presence of an alkali metal hydroxide solution at temperatures between $-20$ and $200°$ C. and a pressure of 1 to 10 bar, in which process for each mole of hal at least 1 mole of alkali metal hydroxide is used.

2. A process for the preparation of a phosphine of the formula

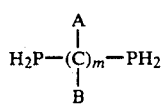

in which m stands for an integer from 2 to 4, and A and B is a straight chain or branched alkyl group having from 1 to 24 carbon atoms, a cycloalkyl, benzyl or allyl group, hydrogen or phenyl group comprising reacting phosphine (PH$_3$) with a reagent of the formula

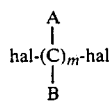

wherein A, B and m have the meaning mentioned and hal is chlorine or bromine, wherein a catalyst selected from the group consisting of tetraalkylammonium and tetraalkylphosphonium salt is added to the reactants and the reaction is conducted in the presence of an aqueous alkali metal hydroxide solution at temperature between $-20$ and $200°$ C. and a pressure of 1 to 10 bar, in which process for each mole of hal at least 1 mole of alkali metal hydroxide is used.

3. The process as claimed in claim 1, wherein the reaction is carried out in the presence of an organic solvent selected from the group consisting of aliphatic and aromatic hydrocarbons having 5 to 16 carbon atoms.

4. The process as claimed in claim 1, wherein the reaction is carried out at temperatures between 0 and $50°$ C.

5. The process as claimed in claim 1, wherein the catalyst is used in concentration of 0.1 to 5 mole %, based on the phosphine used.

6. The process as claimed in claim 1, wherein the alkali metal hydroxide solution is selected from the group of aqueous NaOH and KOH having a concentration of 50 to 70% by weight.

7. The process as claimed in claim 2, wherein the reaction is carried out in the presence of an organic solvent selected from the group consisting of aliphatic and aromatic hydrocarbons having 5 to 16 carbon atoms.

8. The process as claimed in claim 2, wherein the reaction is carried out at temperatures between 0 and $50°$ C.

9. The process as claimed in claim 2, wherein the catalyst is used in a concentration of 0.01 to 5 mole %, based on the phosphine used.

10. The process as claimed in claim 2, wherein the alkali metal hydroxide solution is selected from the group consisting of aqueous NaOH and KOH having a concentration of 50 to 70% by weight.

* * * * *